United States Patent [19]

Lantz et al.

[11] Patent Number: 5,055,624

[45] Date of Patent: Oct. 8, 1991

[54] SYNTHESIS OF 1,1-DICHLORO-1,2,2,2-TETRAFLUOROETHANE

[75] Inventors: Andre Lantz, Vernaison; Bernard Cheminal, Brignais, both of France

[73] Assignee: Atochem, Puteaux, France

[21] Appl. No.: 451,861

[22] Filed: Dec. 18, 1989

[30] Foreign Application Priority Data

Mar. 8, 1989 [FR] France ............................. 8903037

[51] Int. Cl.$^5$ .............................................. C07C 17/08
[52] U.S. Cl. ...................................................... 570/167
[58] Field of Search ................ 570/165, 166, 167, 169

[56] References Cited

U.S. PATENT DOCUMENTS 2,058,453 10/1936 Holt et al. ............................. 570/167
2,748,177 5/1956 Miller et al. ......................... 570/166

FOREIGN PATENT DOCUMENTS 0317981 11/1988 European Pat. Off. .

Primary Examiner—Alan Siegel
Attorney, Agent, or Firm—Morgan & Finnegan

[57] ABSTRACT

The invention relates to the selective manufacture of 1,1-dichloro-1,2,2,2-tetrafluoroethane by catalytic fluorination of 1,1,1-trichloro-2,2,2-trifluoroethane with anhydrous hydrofluoric acid.

The reaction is carried out in the liquid phase at a temperature of between 70° and 170° C. and under a pressure of between 10 and 80 bars absolute, in the presence of an antimony-containing catalyst.

11 Claims, No Drawings

SYNTHESIS OF 1,1-DICHLORO-1,2,2,2-TETRAFLUOROETHANE

FIELD OF THE INVENTION

The invention relates to the selective manufacture of 1,1-dichloro-1,2,2,2-tetrafluoroethane by catalytic fluorination of 1,1,1-trichloro-2,2,2-trifluoroethane in the liquid phase.

BACKGROUND OF THE INVENTION 1,1-Dichloro-1,2,2,2-tetrafluoroethane (also called F114a) is a useful intermediate in the synthesis of 1-chloro-1,2,2,2-tetrafluoroethane, and in particular for that of 1,1,1,2-tetrafluoroethane. The use of which can be envisaged as a substitute for dichlorodifluoromethane.

The production of 1,1-dichloro-1,2,2,2-tetrafluoroethane from 1,1,2-trichloro-1,2,2,-trifluoroethane, hexachloroethane or a mixture of chlorine and tetrachloroethylene by gas-phase processes has already been described in the literature. Thus, for example, in the article by M. Vecchio, et al., Fluorine Chemistry, 4(2), 117–139 (1974) an aluminum fluoride-based catalyst containing small quantities of nickel and/or of chromium is used. The principal disadvantage of this method is its lack of selectivity (joint systematic formation of 1,2-dichloro-1,2,2-tetrafluoroethane, chloropentafluoroethane, and sometimes even hexafluoroethane which has no value) and the risk of the catalyst behaving badly with time. The process according to French Patent No. 1,358,997, which provides for the use of black chrome oxides as catalysts, has the same type of disadvantages.

U.S. Pat. No. 2,748,177 describes in Example 5 a process for the fluorination of 1,1,1-trichloror-2,2,2-trifluoroethane in the gas phase in the presence of a catalyst constituted of aluminum trifluoride. The principal disadvantage of this process is the coproduction of chloropentafluoroethane. According to L. Marangoni, et al., La Chemica e l'Industria, Vol. 64, No. 3, pp. 135–140 (March 1982), a 94.3% yield of 1,1-dichloro-1,2,2,2-tetrafluoroethane could be obtained when fluorinating 1,1,1-trichloro-2,2,2-trifluoroethane in the gas phase using a massive chrome oxide prepared from chrome alum as catalyst. However, the preparation of this catalyst (more particularly its molding) has proved delicate and costly.

Although liquid-phase fluorination in the presence of chlorofluorinated antimony compounds is a known general method, no document describes the use of this method to the selective preparation of 1,1-dichloro-1,2,2,2-tetrafluoroethane. See E. Forche, "Herstellung von Fluorverbindungen", Houben-Weyl 4th Ed., Vol V/3, pp. 126–135; U.S. Pat. Nos. 1,934,943; 1,978,840; 2,005,708 and 2,005,710 and French Patent Nos. 720,474; 730,370; 732,320 and 1,166,833.

On the other hand, it is known that preparation of 1,1,1-trichloro-2,2,2-trifluoroethane (F113a) by isomerization of 1,1,2-trichloro-1,2,2-trifluoroethane (F113) only provides pure F113a with great difficulty, but generally leads to a mixture of the two isomers. The proportion of F113 is capable of being up to 50%, and most often is between 1 and 10%. Now, taking account of the proximity of the boiling points of these isomers (47.6° C. for F113 and 46° C. for F113a) their separation by distillation is difficult to envisage on an industrial scale.

The above references are hereby incorporated by reference.

DETAILED DESCRIPTION OF THE INVENTION

A process for the selective fluorination of F113a to F114a has now been found. It permits such a mixture to be used. It has in fact been ascertained that, working in the liquid phase under certain specific conditions, the isomer F113a can be fluorinated to F114a in a highly selective manner, while, under the same conditions, the isomer F113 undergoes practically no conversion. On the other hand, the formation of by-products such as chloropentafluoroethane (F115) is extremely low, or even zero.

The subject of the invention is therefore a process for the selective preparation of 1,1-dichloro-1,2,2,2-tetrafluoroethane by fluorination of pure 1,1,1-trichloro-2,2,2-trifluoroethane or a mixture of it with 1,1,2-trichloro-1,2,2-trifluoroethane with anhydrous hydrofluoric acid, characterized in that it is carried out in the liquid phase at a temperature of between 70° and 170° C. and under a pressure of between 10 and 80 bars absolute, in the presence of a catalyst constituted by a chlorofluorinated or fluorinated compound of antimony $Sb^v$.

The compounds of antimony $Sb^v$ of formula:

$$SbF_xCl_{5-x}$$

where x is a number ranging from 1 to 5, and preferably 2 to 3, are known fluorination catalysts. They can be obtained in situ or separately under conditions which are known per se, for example in a so-called activation stage according to the following reaction:

$$SbCl_5 + xHF \rightarrow SbF_xCl_{5-x} + xHCl.$$

Antimony pentachloride $SbCl_5$ is itself advantageously formed in situ by chlorination of $SbCl_3$.

The quantity of catalyst to be used, expressed as weight of antimony, can range from 1 to 50 parts per 100 parts of reaction mixture, and is preferably between 5 and 30 parts.

The fluorination according to the invention can be carried out in different manners, for example:
- discontinuously by loading the reagents (HF and F113a or a F113a/F113 mixture) and the catalyst or its precursor ($SbCl_5$ or $SbCl_3 + Cl_2$) into a closed reactor where, as a result of the formation of hydrochloric acid, the pressure increases with the progress of the reaction:
- semi-continuously, working at a constant pressure and removing the hydrochloric acid and all or part of the F114a as they are produced;
- continuously feeding the reagents into the liquid reaction mixture containing the catalyst, and continuously degassing the hydrochloric acid and F114a formed. When working in a continuous manner it is recommended, as is known, that the catalyst is maintained in the active $Sb^v$ form by introducing chlorine.

The fluorination reaction according to the invention can be carried out at a temperature of between 70° and 170° C., but is preferably carried out at a temperature ranging from 90° to 160° C.

The pressure can be between 10 and 80 bars absolute, but must be sufficient to maintain the reagents in the liquid state at the temperature chosen for the reaction.

Without taking account of the hydrofluoric acid which is optionally required for the in situ formation of the catalyst from SbCl5, the molar ratio HF:F113a can range from 1 to 10, and is preferably between 1 and 6. Although selectivity is excellent for these values, it is particularly advantageous to work with a HF:F113a molar ratio of between 1 and 3, in which zone the conversion rate of the F113a is, at the same time, very high. The optimum value of the HF:F113a molar ratio is about 2.

Although it is preferred to work with stirring, good results are also obtained without stirring when the HF:F113a molar ratio is such that the liquid medium is homogenous.

EXAMPLES

In the following examples, which illustrate the invention without implying any limitation, the conversion rate (CR) of the F113a is calculated in the following manner:

$$CR = \frac{(\text{starting moles of } F113a - \text{recovered moles of } F113a)}{\text{starting moles of } F113a} \times 100$$

and the yield (Yd) of F114a with respect to the F113a is expressed as follows:

$$Yd = \frac{\text{moles of } F114a \text{ formed}}{\text{moles of } F113a \text{ converted}} \times 100$$

Example 1

29.6 g (0.1 mole) of antimony pentachloride SbCl5, 58.6 g (0.31 mole) of F113a and 36.6 g (1.83 mole) of liquid anhydrous hydrofluoric acid are loaded into a reactor 0.8 liter in volume, provided with stirring by means of a magnetic bar and with a heating jacket, to give an overall HF:F113a molar ratio of 5.9. The quantity of HF consumed by the catalyst activation reaction being about 0.3 mole. The effective HF:F113a molar ratio is about 5.

After closing the reactor, stirring is started, as is heating in such a manner as to reach the chosen temperature (147° C.) in 2 to 3 hours. Then, while maintaining this temperature and with stirring, the reaction is left to take place until the pressure no longer increases (4 to 5 hours). The reaction mixture is then cooled and degassed. The hydracids are absorbed in water and analyzed to establish their levels. The organic products, entrained by an inert gas, are analyzed by gas phase chromatography after drying over calcium chloride.

The conversion rate (CR) is 55.2%, and the yield of F114a for the F113a converted is 96%. The chloropentafluoroethane (F115) content, if any is formed, is below the detection threshold.

Examples 2 to 7

The experiments were carried out as in Example 1, but modifying the temperature or the overall HF:F113a molar ratio, or removing stirring (Example 7).

Tables I and II, which follow, specify the operating conditions of each experiment and collate the results obtained.

TABLE I

| | Influence of temperature | | |
|---|---|---|---|
| EXAMPLE | 2 | 3 | 4 |
| Operating conditions | | | |
| Overall HF:F113a molar ratio | 5.9 | 5.9 | 5.9 |
| Heating time (hours) | 2.3 | 2.3 | 2.3 |
| Reaction time (hours) | 5.1 | 5.0 | 5.0 |
| Temperature (°C.) | 117 | 137 | 158 |
| Pressure (bars absolute) | 32.5 | 44.0 | 50.0 |
| Results | | | |
| CR (%) | 15.2 | 35.6 | 61.3 |
| Yd (%) | 94.7 | 98.3 | 99.7 |

TABLE II

| | Effect of HF:F113a molar ratio | | | |
|---|---|---|---|---|
| EXAMPLE | 5 | 6 | 7 | 1 |
| Operating conditions | | | | |
| Overall HF:F113a molar ratio | 2.1 | 2.9 | 2.9 | 5.9 |
| Heating time (hours) | 2.3 | 2.5 | 2.3 | 2.3 |
| Reaction time (hours) | 5.0 | 4.8 | 5.0 | 5.0 |
| Temperature (°C.) | 147 | 148 | 144 | 147 |
| Pressure (bars absolute) | 36.6 | 42.0 | 39.5 | 49.0 |
| Results | | | | |
| CR (%) | 85.5 | 90.5 | 92.3 | 55.2 |
| Yd (%) | 99.2 | 99.8 | 99.6 | 96.0 |

In Examples 6 and 7, molar contents of F115 of 0.02% and 0.1% respectively were detected. In the other examples, the presence of F115 could not be detected (content zero or below the detection threshold).

Example 8 (Comparative)

The process is as in the previous examples, but replacing the F113a with F113, and working with stirring in the following conditions:
overall HF:F113 molar ratio: 5.9
heating time: 2.4 hours
reaction time: 4.9 hours
temperature: 151° C.
pressure: 46.5 bars absolute The organic mixture obtained after degassing the reactor contains, in moles, 99.6% of F113 and 0.4% of F114 (1,2-dichloro-1,1,2,2-tetrafluoroethane).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Process for the selective preparation of 1,1-dichloro-1,2,2,2-tetrafluoroethane by fluorination of pure 1,1,1-trichloro-2,2,2-trifluoroethane or a mixture of it with 1,1,2-trichloro-1,2,2-trifluoroethane with anhydrous hydrofluoric acid, comprising carrying out the fluorination in the liquid phase at a temperature of between 70° and 170° C. and under a pressure of between 10 and 80 bars absolute, in the presence of a catalyst comprising an antimony compound of formula $SbF_xCl_{5-x}$, x being a number ranging from 1 to 5.

2. The process according to claim 1, wherein the effective hydrofluoric acid: 1,1,1-trichloro-2,2,2-trifluoroethane molar ratio is between 1 and 3.

3. The process according to claim 2, wherein the molar ratio is about 2.

4. The process according to claim 1, wherein the fluorination is carried out at a temperature ranging from 90° to 160° C.

5. The process according to claim 1, wherein 1 to 50 parts by weight of antimony are used per 100 parts of reaction mixture.

6. The process according to claim 5, wherein 5–30 parts by weight of antimony are used per 100 parts of reaction mixture.

7. The process according to claim 1, wherein the catalyst $SbF_xCl_{5-x}$ is formed in situ from antimony pentachloride or from a mixture of antimony trichloride and chlorine.

8. The process according to claim 1, wherein x is a number ranging from 2 to 3.

9. The process according to claim 1, wherein the process is carried out continously and the catalyst is maintained in the active $Sb^v$ form by the introduction of chlorine.

10. The process according to claim 1, further comprising starting with a mixture of 1,1,1-trichloro-2,2,2-trifluoroethane and 1,1,2-trichloro-1,2,2-trifluoroethane the proportion of the latter being up to 50%.

11. The process according to claim 10, wherein the proportion being less than 10%.

* * * * *